(12) United States Patent
Molenda et al.

(10) Patent No.: US 10,603,258 B2
(45) Date of Patent: Mar. 31, 2020

(54) CLEANSING COMPOSITION

(71) Applicant: KAO Germany GmbH, Darmstadt (DE)

(72) Inventors: Michael Molenda, Frankfurt (DE); Ilka Tietjen, Ilvesheim (DE); Eiji Terada, Tokyo (JP)

(73) Assignee: KAO GERMANY GMBH, Darmstadt (DE)

( * ) Notice: Subject to any disclaimer, the term of this patent is extended or adjusted under 35 U.S.C. 154(b) by 171 days.

(21) Appl. No.: 15/398,235

(22) Filed: Jan. 4, 2017

(65) Prior Publication Data
US 2017/0112739 A1    Apr. 27, 2017

Related U.S. Application Data

(63) Continuation of application No. 13/062,017, filed as application No. PCT/EP2009/006347 on Sep. 2, 2009, now abandoned.

(51) Int. Cl.
| | |
|---|---|
| *A61K 8/19* | (2006.01) |
| *A61Q 5/12* | (2006.01) |
| *A61Q 5/06* | (2006.01) |
| *A61Q 5/02* | (2006.01) |
| *A61K 8/34* | (2006.01) |
| *A61K 8/04* | (2006.01) |
| *A61K 8/44* | (2006.01) |

(52) U.S. Cl.
CPC ............ *A61K 8/19* (2013.01); *A61K 8/046* (2013.01); *A61K 8/342* (2013.01); *A61K 8/44* (2013.01); *A61Q 5/02* (2013.01); *A61Q 5/065* (2013.01); *A61Q 5/12* (2013.01); *A61K 2800/432* (2013.01)

(58) Field of Classification Search
CPC .......... A61K 8/19; A61K 8/342; A61K 8/046; A61K 8/44; A61Q 5/12; A61Q 5/065; A61Q 5/02
See application file for complete search history.

(56) References Cited

U.S. PATENT DOCUMENTS

2006/0251602 A1* 11/2006 Goddinger ............. A61K 8/342
424/70.13
2007/0031365 A1* 2/2007 Terada .................. A61K 8/891
424/70.122

* cited by examiner

*Primary Examiner* — Ali Soroush
*Assistant Examiner* — Genevieve S Alley
(74) *Attorney, Agent, or Firm* — Norris McLaughlin, P.A.

(57) ABSTRACT

An aqueous cleansing composition for keratin fibres comprises at least one amino acid surfactant and an aqueous emulsion of divinyldimethicone/dimethicone copolymer. The amino acid surfactant 3 of the following structure

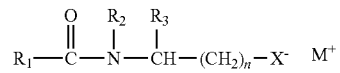

wherein $R_1$ is a saturated or unsaturated, straight or branched alkyl chain with 7 to 17 C atoms, $R_2$ is H or a methyl, $R_3$ is H, $COO^- M^+$, $CH_2COO^-M$ or COOH, n is 0 to 2, X is $COO^-$ or $SO_3^-$ and M is independent from each other H, sodium or potassium, and an aqueous emulsion of divinyldimethicone/dimethicone copolymer with an internal phase viscosity of more than $1\times10^8$ mm$^2$/s measured at 0.01 Hz at about 25° C.

11 Claims, No Drawings

CLEANSING COMPOSITION

This is a Continuation application of U.S. Ser. No. 13/062,017 filed 3 Mar. 2011, which in turn was an a 371 application of PCT/EP2009/006347 filed Sep. 2, 2009, which claimed foreign priority benefit under 35 U.S.C. § 119 of European Application No. 08015668.0 filed 5 Sep. 2008.

The present invention is related to an aqueous cleansing composition for keratin fibres, especially human hair, comprising at least one amino acid surfactant, at least one alkyl glyceryl ether and at least one fatty alcohol.

Cleansing compositions have been known for many years. Many patent applications and scientific publications deal with such compositions aiming at cleansing and especially improved conditioning effects. On the other hand, attempts have been made to improve foam quality of cleansing compositions in terms of its volume and its creaminess. However there is still need for further improvements.

EP 1 696 023 A1 discloses surfactant compositions comprising alkyl ether sulphate type of surfactant, glyceryl ether or diglyceryl ether and a water soluble salt. The document is silent on amino acid surfactants.

WO 2004/014334 A1 is on hair detergent compositions comprising anionic surfactant, monoalkyl or monoalkenyl glyceryl ether and silicone conditioning agent. Nothing is disclosed on amino acid surfactants.

EP 1 221 474 A1 is as well on detergent compositions comprising anionic phosphate surfactants and glyceryl ether. Amino acid surfactants are not mentioned at all.

Aim of the present invention is to provide a cleansing composition having improved foam properties in terms of its volume and creaminess as well as improved conditioning effects on keratin fibres, especially human hair, in terms of combability, smoothness, elasticity, softness, volume and body.

Present inventors have surprisingly found that a cleansing composition comprising at least one amino acid surfactant, at least one mono or dialkyl glyceryl ether and at least one fatty alcohol provides excellent foam performance observed as improved foam creaminess and foam volume.

Accordingly, the first object of the present invention is a cleansing composition comprising at least one amino acid surfactant of the following structure

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or $COOH$, n is 0 to 2, X is $COO^-$ or $SO_3^-$ and M is independent from each other H, sodium or potassium, at least one glyceryl ether of the following formula

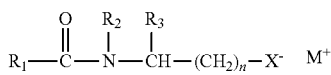

wherein $R_4$ is straight or branched, saturated or unsaturated alkyl chain with 4 to 24 C atoms and $R_5$ is H, or straight or branched, saturated or unsaturated alkyl chain with 4 to 24 C atoms, and at least one fatty alcohol of the following formula $R_6$—OH wherein $R_6$ is straight or branched, saturated or unsaturated alkyl chain with 8 to 24 C atoms.

With the term amino acid surfactants especially those surfactants are meant derived from taurate, glucamate, alanin or alaninate, sarcosinate and aspartate.

Second object of the present invention is the use of cleansing composition comprising at least one amino acid surfactant of the above general formula, at least one glyceryl ether of the above general formula and at least one fatty alcohol of the above general formula for cleansing hair.

Third objective of the present invention is the use of at least one amino acid surfactant of the above general formula, at least one glyceryl ether of the above general formula and at least one fatty alcohol of the above general formula for increasing foam volume and for improving foam creaminess of the cleansing compositions based on at least one anionic surfactant and optionally comprising non-ionic and amphoteric surfactants.

Cleansing composition of the present invention comprises at least one amino acid surfactant according to the general formula given above at a concentration of 0.1 to 15%, by weight, calculated to total composition. Preferably, the concentration of amino acid surfactant is from 0.25 to 10% by weight, more preferably 0.5 to 7.5% by weight and most preferably 1 to 5% by weight, calculated to total composition. The concentrations mentioned here are total concentration ranges in case more than one amino acid surfactant is present. In the preferred embodiment of the present invention $R_1$ in the general formula of amino acid surfactants disclosed above is a saturated or unsaturated, straight or branched alkyl chain with 9 to 17 C atoms, and more preferably 9 to 13 C atoms, $R_2$ is H or a methyl, $R_3$ is H, $COO^-M^+$, $CH_2COO^-M$ or $COOH$, n is 0 to 2, X is $COO^-$ or $SO_3^-$ and M is independent from each other H, sodium or potassium. It should be noted that alkyl chain includes also mixture of various alkyl groups as present especially in plant triglyceride derived alkyl chains such as cocoyl chain.

Suitably amino acid surfactant types are taurate, glutamate, alanin or alaninate, sarcosinate, aspartate surfactants, and mixtures thereof. Preferred are taurate, glutamate and sarcosinate surfactants and mixtures thereof. More preferred are taurates and glutamates and most preferred is glutamate type surfactants.

Suitable taurate surfactants are according to the general formula

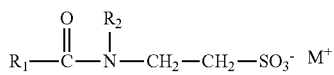

wherein $R_1$ is preferably a saturated or unsaturated, straight or branched alkyl chain with 7 to 17 C atoms, and more preferably 9 to 13 C atoms, $R_2$ is H or methyl, and M is H, sodium or potassium. Suitable examples are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, and sodium methyl stearoyl taurate and mixtures thereof. Preferred are potassium cocoyl taurate, potassium methyl cocoyl taurate, sodium caproyl methyl taurate, sodium cocoyl taurate, sodium lauroyl taurate, sodium methyl cocoyl taurate and sodium methyl lauroyl taurate and mixtures thereof. More preferred are potassium cocoyl taurate, potassium methyl cocoyl taurate, sodium cocoyl taurate, sodium lauroyl taurate, sodium methyl cocoyl taurate and sodium methyl lauroyl taurate and mixtures thereof.

Suitable glutamate surfactants are according to the general formula

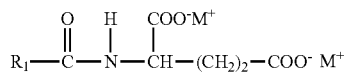

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, and sodium lauroyl glutamate and mixtures thereof.

Suitable alanine or alaninate surfactants are according to the general formula

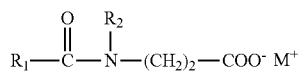

wherein $R_1$ is preferably a saturated or unsaturated, straight or branched alkyl chain with 7 to 17 C atoms, and more preferably 9 to 13 C atoms, $R_2$ is H or methyl and M is H, sodium or potassium. Suitable examples are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine and mixtures thereof.

Suitable glycine surfactants are according to the general formula

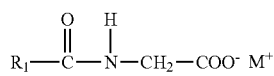

wherein $R_1$ is preferably a saturated or unsaturated, straight or branched alkyl chain with 7 to 17 C atoms, and more preferably 9 to 13 C atoms, and M is H, sodium or potassium. Suitable examples are palmitoyl glycine, sodium lauroyl glycine, sodium cocoyl glycine, sodium myristoyl glycine, potassium lauroyl glycine, and potassium cocoyl glycine and mixtures thereof.

Suitable sarcosinate surfactants are according to the general formula

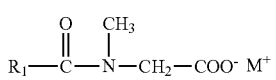

wherein $R_1$ is preferably a saturated or unsaturated, straight or branched alkyl chain with 7 to 17 C atoms, and more preferably 9 to 13 C atoms, and M is H, sodium or potassium. Suitable examples are potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof. Preferred are potassium lauroyl sarcosinate, potassium cocoyl sarcosinate, sodium cocoyl sarcosinate, and sodium lauroyl sarcosinate and mixtures thereof. More preferred are sodium cocoyl sarcosinate, and sodium lauroyl sarcosinate and mixtures thereof.

Suitable aspartate surfactants are according to the general formula

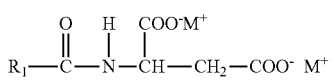

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, and dipotassium caproyl aspartate and mixtures thereof. Preferred are sodium lauroyl aspartate, sodium myristoyl aspartate, sodium cocoyl aspartate, and sodium caproyl aspartate and mixtures thereof.

It should be noted that compositions of the present invention can also comprise mixture of several type of amino acid surfactants such as mixture of glutamate and taurate surfactants, or mixture of taurate, glutamate and sarcosinate surfactants etc.

Cleansing compositions of the present invention comprise at least one anionic surfactant at a concentration range of 1 to 25%, preferably 2 to 20% and more preferably 2.5 to 20%, and most preferably 5 to 15% by weight, calculated to the total composition.

Within the scope of the present invention, with the term anionic surfactant it is meant any anionic surfactant other than amino acid surfactants.

In principal any anionic surfactant is suitable within the meaning of the present invention. As mentioned above with the term anionic surfactant any anionic surfactants are meant other than amino acid surfactants. Nonlimiting examples are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

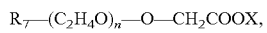

wherein $R_7$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

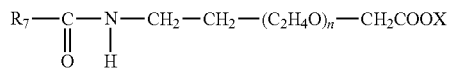

wherein R and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

The most preferred anionic surfactants within the meaning of the present invention are those of alkyl ether sulphates such as lauryl ether sulphate sodium salt.

In a preferred embodiment of the present invention, cleansing composition of the present invention comprises at least one anionic surfactant as mentioned above and at least one nonionic surfactant. Nonionic surfactants are suitable at a concentration of 1% to 15%, in particular from 1% to 10% by weight, calculated to the total composition.

Nonionic surfactants especially suited in the cleansing compositions according to the invention are alkyl polyglucosides of the general formula

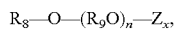

wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5.

These alkyl polyglucosides are known in particular as excellent skin-compatible, foam improving agents in liquid detergents and body cleansing compositions. Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactants are, suitable for the cleansing compositions of the present invention, long-chain fatty acid dialkanolamides, such as coco fatty acid diethanolamide and myristic fatty acid diethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylate. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

The most preferred non-ionic surfactants are alkyl polyglucosides such as decyl, cocoyl polyglucoside and ethoxylated fatty alcohols such as laureth-16.

In a further preferred embodiment of the present invention, cleansing composition of the present invention comprises at least one anionic, at least one nonionic surfactant and at least one amphoteric or zwitterionic surfactant.

Amphoteric or zwitterionic surfactants, are present at a concentration of 0.5% to about 15%, preferably 1% to about 10%, by weight, calculated to the total composition. It has especially been found out that addition of zwitterionic or amphoteric surfactants enhances foam feeling in terms of creaminess, foam volume and as well as skin compatibility are also improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, suitable betaine surfactants are of general structure

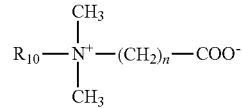

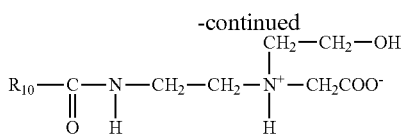

wherein $R_{10}$ is a $C_8$-$C_{18}$-alkyl group and n is 1 to 3;
sulfobetaines of the structure

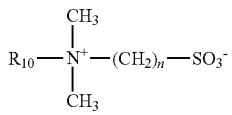

wherein $R_{10}$ and n are same as above;
and amidoalkyl betaines of the structure

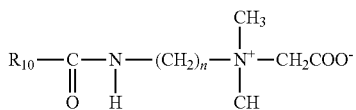

wherein $R_{10}$ and n are same as above.

The most preferred amphoteric surfactants are alkyl betaines such as lauryl betaine and alkyl amido betaines such as cocamidopropyl betaine.

In a further preferred form of the present invention, cleansing composition comprises at least one anionic surfactant especially of alkyl ether sulphate type, at least one amphoteric surfactant especially alkyl amido alkyl betaine type and at least one non-ionic surfactant especially an alkyl polyglucoside type in the above mentioned concentration ranges.

Aqueous cleansing composition of the present invention comprises at least one glyceryl ether of the following formula

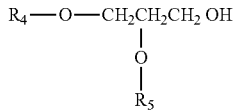

wherein $R_4$ is straight or branched, saturated or unsaturated alkyl chain with 4 to 24 C atoms, preferably 4 to 18 and more preferably 4 to 12 C atoms and $R_5$ is H, or straight or branched, saturated or unsaturated alkyl chain with 4 to 24 C atoms, 4 to 18 and more preferably 4 to 12 C atoms and most preferably $R_5$ is H, at a concentration of 0.1 to 15%, preferably 0.1 to 10% and more preferably 0.25 to 7.5% and most preferably 0.5 to 5% by weight calculated to total composition.

Suitable unlimited examples are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Most preferred are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether are glyceryl lauryl ether, and their mixtures.

It should be noted that within the disclosure of the present description, glyceryl decyl ether is used as synonym of decyl glycerine. For the other compounds in the above paragraph the same is valid.

Aqueous cleansing composition of the present invention comprise at least one fatty alcohol of the following formula $$R_6\text{—OH}$$

wherein $R_6$ is straight or branched, saturated or unsaturated alkyl chain with 8 to 24, preferably 10 to 22, more preferably 12 to 18 and most preferably 12 to 16 C atoms at a concentration of 0.1 to 5%, preferably 0.1 to 4% and more preferably 0.25 to 3% and most preferably 0.5 to 2.5% by weight calculated to total composition.

Suitable non-limiting preferred examples are decyl alcohol, myristyl alcohol, lauryl alcohol, cetyl alcohol, stearyl alcohol, behenyl alcohol, and arachidyl alcohol and their mixtures. More preferred are decyl alcohol, myristyl alcohol, lauryl alcohol, cetyl alcohol, and stearyl alcohol. Most preferred are decyl alcohol, myristyl alcohol and lauryl alcohol, and their mixtures.

In a further preferred embodiment, cleansing composition of the present invention comprises hair-conditioning agents. Conditioning agents can be selected from oily substances, non-ionic substances, cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule such as trimethyl pentaphenyl trisiloxane, natural oils such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents can be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_{11}CO(OCH_2CH_2)_nOH \text{ or}$$

$$R_{11}CO(OCH_2CH_2)_nOOCR_{12}$$

where $R_{11}$ and $R_{12}$ are independent from each other saturated, unsaturated or branched or non-branched alkyl chain with 7 to 21 C atoms and n is typically 2-100.

In one of the preferred form of the present invention, cleansing compositions comprise at least one cationic polymer as conditioning agent. Suitable cationic polymers are those of best known with their CTFA category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhone-Poulenc which are chemically for example Guar hydroxypropyl trimonium chloride and cationic tara gum an its derivatives known with INCI name Caesalpinia spinosa hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic Caesalpinia spinosa gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Although less preferred, cleansing compositions of the present invention may comprise additionally one or more cationic surfactant(s) as conditioner presented with the general formula

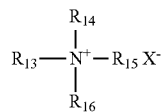

where $R_{13}$ is a saturated or unsaturated, branched or non-branched alkyl chain with 8-24 C atoms or $R_{17}CONH(CH_2)_n$ where $R_{17}$ is saturated or unsaturated, branched or non-branched alkyl chain with 7-21 C atoms and n has value of 1-4, or $R_{18}COO(CH_2)_n$ where $R_{18}$ is saturated or unsaturated, branched or non-branched alkyl chain with 7-21 C atoms and n has value of 1-4, and $R_{14}$ is hydrogen or unsaturated or saturated, branched or non-branched alkyl chain with 1-24 C atoms or $R_{17}CONH(CH_2)_n$ or $R_{18}COO(CH_2)_n$ where $R_{17}$, $R_{18}$ and n are same as above.

$R_{15}$ and $R_{16}$ are hydrogen or lower alkyl chain with 1 to 4 carbon atoms which may be substituted with one or more hydroxyl groups, and X is anion such as chloride, bromide, methosulfate.

Typical examples of those ingredients are cetyl trimethly ammonium chloride, stear trimonium chloride, behentrimonium chloride, stearamidopropyl trimonuim chloride, dioleoylethyl dimethyl ammonium methosulfate, dioleoylethyl hydroxyethylmonium methosulfate.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, silicone oil and derivatives and cationic surfactants is in the range of 0.01 to 5% by weight, preferably 0.01 to 3.5% by weight, more preferably 0.05 to 2.5% and most preferably 0.1 to 1.5% by weight calculated to the total composition. Most preferred conditioning agents are cationic polymers.

In another preferred form of the invention, aqueous cleansing composition comprises at least one organic solvent such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, polypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzyl alcohol and polypropylene glycols. Total concentration of organic solvents in the shampoo composition should not exceed 5% by weight, preferably in the range of 0.1 to 3%, more preferably 0.5 to 2.5% by weight calculated to total composition.

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning shampoo composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl methacrylates of the type "Yukaformer®", e.g., the butyl methacrylate copolymer "Yukaformer® Am75"; copolymers from monomers containing carboxyl groups and sulfonic groups, e.g., (meth)acrylic acid and itaconic acid, with monomers such as mono- or dialkyl amino alkyl(meth)acrylates or mono- or dialkyl aminoalkyl (meth)acrylamides containing basic groups, in particular amino groups; copolymers from N-octyl acrylamide, methyl methacrylate, hydroxypropyl methacrylate, N-tert.-butyl aminoethyl-methacrylate and acrylic acid, as well as the copolymers known from U.S. Pat. No. 3,927,199, are applicable.

Cleansing composition of the present invention are preferably pearly. Pearl-shiny appearance is achieved with those dispersed in cleansing conditioning compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kinds of mixtures are available commercially.

Solubilizers may be added to the compositions especially when oily substances are chosen as conditioning agents and fragrance oils with highly lipophilic properties. Typical solubilizers may be hydrogenated castor oil known with the trade mark Cremophor CO series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The cleansing composition may contain active ingredients selected from UV filters, moisturizers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are preferably selected from polycarboxy acids. The preferred one is ethylene diamine tetraacetic acid, EDTA. Typical useful concentration range for sequestering agents is of 0.01-2.5% by weight calculated to the total composition.

The UV filters are that oil and water soluble ones for the purpose of protecting hair and hair colour. In other words, anionic and non-ionic, oily, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2.2',4,4'-tetrahydroxy-benzophenone, 2-hydroxy-4-methoxy-benzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecamphor, 3-(4'-sulfo)-benzyl-idenebornane-2-one and the salts thereof, 3-(4'-methyl benzylidene)-DL-campher, and/or polysilicone-15. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, various "Extrapone®" products, and "Herbasol®". Extracts and the preparation thereof are also described in "Hagers Handbuch der pharmazeutischen Praxis", 4$^{th}$ Ed., Compositions of the present invention may comprise further at least one compound according to the formula

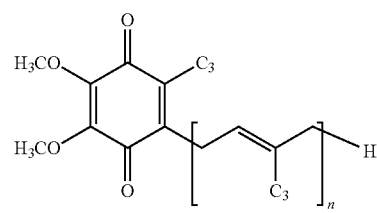

where n is a number from 1 to 10.

The compounds of the above formula are known as Ubiquinone, and also are known as Coenzyme. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Cleansing compositions of the present invention can also comprise synthetic mica as a further shine enhancer.

Suitable metal oxide or oxides for coating synthetic mica are titanium dioxide, chromium oxide, ferric oxide or mixtures thereof. In the present invention the preferred is synthetic mice coated with titanium dioxide. Such materials are commercially available from Sun Chemical Corporation and known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.20 to 2.5% by weight calculated to total composition.

Further in a preferred embodiment of the present invention, compositions comprise at least one direct dye. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuff categories is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and mixtures thereof.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and mixtures thereof.

Among those, the preferred anionic dyestuffs are Acid Red 52, Acid Violet 2, Acid Red 33, Acid Orange 4, Acid Red 27 and Acid Yellow 10 and their salts, and mixtures thereof. The most preferred anionic dyes are Acid Red 52, Acid Violet 2, Acid Red 33, Acid Orange 4 and Acid Yellow 10, and their salts, and mixtures thereof.

Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and mixtures thereof.

Concentration of one or more direct dyes in total is in the range of 0.001 to 5% by weight, preferably 0.01 to 4% more preferably 0.05 to 3% and most preferably 0.1 to 2.5% by weight calculated to total composition. The most preferred among the direct dyes is cationic direct dyes.

It is self-understood that the shampoos according to the invention may comprise other substances customarily used in such compositions such as preservatives, fragrances.

The pH of the compositions according to the present invention is suitably between 2 and 8.0, preferably in the range of 2.5 to 7.0, more preferably 3 to 6.5 and most preferably 4 to 5.5 measured at ambient temperature with a suitable pH meter.

pH of the compositions is adjusted with acidic and alkaline compounds. Acidic compounds can be inorganic and organic acid or their mixtures. Nonlimiting suitable examples are citric acid, lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Alkaline compounds such as sodium hydroxide can be used to adjust the pH of the compositions.

Aqueous cleansing composition of the present invention preferably comprises one or more thickeners. Suitable ones are ethoxylated polyglyceryl esters with total ethoxy units in the range of 50 to 200 and fatty acyl chain length of 8 to 22 C atoms such as PEG-80 glyceryl cocoate, PEG-90 glyceryl isostearate, PEG-120 glyceryl stearate, PEG-200 glyceryl stearate, PEG-80 glyceryl tallowate, PEG-82 glyceryl tallowate, PEG-130 glyceryl tallowate, and PEG-200 glyceryl tallowate, glyceryl oleate/cocoate and inorganic salt in particular sodium chloride when especially composition comprise alkyl ether sulphate type of surfactants.

Cleansing compositions of the present invention preferably has a viscosity in the range of 500 to 20,000 mPa·s, more preferably 1,000 to 15,000 mPa·s and most preferably 1,500 to 10,000 mPa·s measured at 20° C. with a Brookfield viscosimetre using for example Spindle 5 at appropriate rotation speed.

The following examples are to illustrate the invention, but not to limit. The products according to the invention are prepared by mixing the individual components in water, whereby it is also possible to use pre-mixtures of various ingredients.

EXAMPLE 1

TABLE I

Comparative aqueous cleansing compositions

| | % by weight | | | | |
|---|---|---|---|---|---|
| | A | B | C | D | E |
| Sodium laureth sulfate | 12 | 12 | 12 | 12 | 12 |
| Cocamidopropyl betaine | 3 | 3 | 3 | 3 | 3 |
| Coco glucoside | 1.5 | 1.5 | 1.5 | 1.5 | 1.5 |

TABLE I-continued

Comparative aqueous cleansing compositions

| | % by weight | | | | |
|---|---|---|---|---|---|
| | A | B | C | D | E |
| Sodium lauroyl glutamate | — | 1 | — | — | 0.5 |
| Ethylhexyl glycerin | — | — | 1 | — | 0.5 |
| Myristyl alcohol | — | — | — | 1 | 1 |
| Guar hydroxypropyl trimonium chloride | 0.5 | 0.5 | 0.5 | 0.5 | 0.5 |
| Bis(C13-15 Alcoxy PG-Amodimethocne | 0.4 | 0.4 | 0.4 | 0.4 | 0.4 |
| Citric acid | | | q.s to pH 5.0 | | |
| Preservative, fragrance | | | q.s. | | |
| Water | | | q.s. to 100 | | |

Shampoo composition E is according to the invention and A to D represent comparative compositions.

Foam speed, foam stability and foam creaminess were measured as follows.

Foam speed: A shampoo solution was prepared in tap water at a concentration of 20% by weight. The solution was mixed with a propeller at 100 rpm for 2 min and left for 4 min without mixing. Afterwards foam volume (ml) was measured in the same cylinder.

Foam stability: 35 g of the foam obtained with foam speed test was placed on a filter in a funnel and volume of liquid collected in a cylinder was measured after 30 min.

Foam creaminess: 10 volunteers were asked to judge creaminess by hand.

Results are presented in Table II.

TABLE II

Results of the foam volume, foam speed and foam creaminess tests

| | A | B | C | D | E |
|---|---|---|---|---|---|
| Foam speed | 310 | 360 | 380 | 320 | 440 |
| Foam stability | 25 | 21 | 22.5 | 19.5 | 14 |
| Foam creaminess | 0 | 0 | 1 | — | 9 |

From the above results, it was concluded that the inventive composition showed the highest foam volume, the highest foam speed and the foam was the creamiest. The effect is synergistic since sum of the effects of the individual components is less than the effect observed in combination.

EXAMPLE 2

| | % by weight |
|---|---|
| Sodium lauryl ether sulphate | 12.6 |
| Sodium lauroyl glutamate | 1.5 |
| Ethylhexyl glycerine | 1.0 |
| Myristyl alcohol | 0.5 |
| PEG-90 glyceryl isostearate | 3.0 |
| Citric acid/sodium hydroxide | q.s. to pH 5.5 |
| Preservative, fragrance | q.s |
| Water | to 100 |

The above shampoo was judged to have rich and creamy foam in a monadic test by the volunteers. It was furthermore mentioned that it foams very quickly.

EXAMPLE 3

| | % by weight |
|---|---|
| Sodium lauryl ether sulphate | 9.0 |
| Cocyl glucoside | 4.0 |
| Sodium lauroyl glutamate | 2.0 |
| Ethylhexyl glycerine | 0.8 |
| Lauryl alcohol | 1.0 |
| Polyquaternium-7 | 1.0 |
| PEG-18 Glyceryl oleate/cocoate | 1.0 |
| Citric acid/sodium hydroxide | q.s. to pH 5.5 |
| Preservative, fragrance | q.s |
| Water | to 100 |

The above composition has excellent creamy rich foam and conditions hair excellently in terms of combability and soft hair feeling.

EXAMPLE 4

| | % by weight |
|---|---|
| Sodium lauryl ether sulfate | 9.0 |
| Cocyl glucoside | 3.0 |
| Cocoyl betaine | 2.0 |
| Sodium lauroyl glutamate | 2.0 |
| Ethylhexyl glycerine | 1.5 |
| Lauryl alcohol | 0.7 |
| Polyquaternium-10 | 0.5 |
| Dimethicone | 0.5 |
| Ubiquinone | 0.1 |
| Sodium chloride | 1.2 |
| PPG-9 | 2.0 |
| Citric acid/sodium hydroxide | q.s. to pH 5.0 |
| Preservative, fragrance | q.s |
| Water | to 100 |

The above composition improves hair volume, gives hair more elasticity in addition to the excellent creamy foam and conditioning effect in terms of combability, shine and soft hair feeling.

EXAMPLE 5

| | % by weight |
|---|---|
| Sodium lauryl ether sulphate | 8.0 |
| Cocoyl polyglucoside | 1.5 |
| Cocamidopropyl betaine | 4.0 |
| Sodium cocoyl glutamate | 2.0 |
| Decyl glycerine | 1.0 |
| Decyl alcohol | 1.0 |
| Polyquaternium-7 | 0.8 |
| Dimethicone | 0.5 |
| PEG-160 sorbitan triisostearate | 1.0 |
| PPG-9 | 1.2 |
| Basic red 51 | 0.1 |
| Citric acid/sodium hydroxide | q.s. to pH 5.5 |
| Preservative, fragrance | q.s |
| Water | to 100 |

The above composition gives hair a red shine, and additionally delivers excellent conditioning effect in terms of more elasticity, combability, shine and soft hair feeling in addition to the excellent creamy rich foam. The composition foams very quickly.

EXAMPLE 6

| | % by weight |
|---|---|
| Sodium lauryl ether sulfate | 9.0 |
| Laureth-16 | 3.0 |
| Cocoyl betaine | 2.0 |
| Sodium cocoyl glutamate | 2.0 |
| Guarhydroxypropyltrimonium chloride | 1.0 |
| Sodium chloride | 1.0 |
| Heptyl glycerine | 0.7 |
| Myristyl alcohol | 0.5 |
| PPG-9 | 1.0 |
| Trimethyl pentaphenyl trisiloxane | 0.3 |
| Basic yellow 87 | 0.08 |
| Basic red 76 | 0.001 |
| Citric acid/sodium hydroxide | q.s. to pH 5.0 |
| Preservative, fragrance | q.s |
| Water | to 100 |

Excellent conditioning effects were observed in terms of volume, combability, elasticity and manageability and additionally an excellent golden blonde shine was observed on light blond hair. Excellent foam quality in terms of speed, volume and creaminess was observed in a monadic test.

EXAMPLE 7

| | % by weight |
|---|---|
| Sodium lauryl ether sulfate | 9.0 |
| Cocyl glucoside | 3.0 |
| Lauryl betaine | 2.0 |
| Sodium cocoyl glutamate | 2.0 |
| Guarhydroxypropyltrimonium chloride | 1.0 |
| PEG-80 glyceryl oleate/cocoate | 1.0 |
| Ethylhexyl glycerine | 1.0 |
| Myristyl alcohol | 1.0 |
| PPG-9 | 1.0 |
| Trimethyl pentaphenyl trisiloxane | 0.3 |
| Basic red 51 | 0.1 |
| Basic orange 31 | 0.05 |
| Citric acid/sodium hydroxide | q.s. to pH 5.0 |
| Preservative, fragrance | q.s |
| Water | to 100 |

Excellent red shine were observed on medium blond hair, in addition to excellent foam characteristics in terms of speed, volume and creaminess in a monadic test.

EXAMPLE 8

| | % by weight |
|---|---|
| Sodium lauryl ether sulfate | 9.0 |
| Laureth-16 | 3.0 |
| Cocoyl betaine | 2.0 |
| Sodium cocoyl glutamate | 2.0 |
| Ethylhexyl glycerine | 1.0 |
| Myristyl alcohol | 1.0 |
| Polyquaternium-10 | 1.0 |
| PEG-90 glyceryl isostearate | 3.5 |
| PPG-9 | 0.7 |
| Carbopol Aqua CC | 5.0 |
| Synthetic fluorphologopite* | 0.5 |
| Citric acid/sodium hydroxide | q.s. to pH 4.7 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 μm.

The above composition delivered excellent volume and shine to dark blonde fine hair. Foam characteristics were found to be excellent in terms of volume, speed and creaminess in a monadic test.

EXAMPLE 9

| | % by weight |
|---|---|
| Sodium lauryl ether sulfate | 10.0 |
| Cocoyl betaine | 2.0 |
| Decyl glucoside | 1.5 |
| Sodium lauroyl glutamate | 4.0 |
| Ethylhexyl glycerine | 1.0 |
| Myristyl alcohol | 1.0 |
| Quaternium 80 | 0.5 |
| Polyquaternium-7 | 0.2 |
| Sodium chloride | 1.0 |
| PPG-9 | 1.7 |
| Citric acid/sodium hydroxide | q.s. to pH 5.0 |
| Preservative, fragrance | q.s |
| Water | to 100 |

Above shampoo was found to be excellent volume giving shampoo to fine hair in a monadic test in addition to the excellent foam characteristics as in the previous examples.

With the following examples similar results were found as in the previous examples in hair conditioning and foam characteristics.

EXAMPLE 10

| | % by weight |
|---|---|
| Sodium lauryl ether sulphate | 8.0 |
| Cocoyl polyglucoside | 2.0 |
| Cocamidopropyl betaine | 4.0 |
| Ethylhexyl glycerine | 1.0 |
| Myristyl alcohol | 1.0 |
| Sodium cocoyl glutamate | 2.0 |
| Trimethyl pentaphenyl trisiloxane | 0.3 |
| Polyquaternium-7 | 1.0 |
| PEG-120 glyceryl stearate | 3.0 |
| PPG-15 | 1.7 |
| Citric acid/sodium hydroxide | q.s. to pH 5.2 |
| Preservative, fragrance | q.s |
| Water | to 100 |

EXAMPLE 11

| | % by weight |
|---|---|
| Sodium lauryl ether sulphate | 8.0 |
| Cocoyl glucoside | 5.0 |
| Cocamidopropyl betaine | 4.0 |
| Sodium cocoyl glutamate | 2.0 |

-continued

| | % by weight |
|---|---|
| Ethylhexyl glycerine | 1.0 |
| Myristyl alcohol | 1.0 |
| Polyquaternium-7 | 1.0 |
| PEG-90 glyceryl isostearate | 1.5 |
| PEG-30 glyceryl isostearate | 1.5 |
| PPG-15 | 0.3 |
| PPG-9 | 0.8 |
| Citric acid/sodium hydroxide | q.s. to pH 5.2 |
| Preservative, fragrance | q.s |
| Water | to 100 |

EXAMPLE 12

| | % by weight |
|---|---|
| Sodium lauryl ether sulphate | 5.0 |
| Sodium lauryl ether carboxylate | 3.0 |
| Laureth-16 | 3.0 |
| Cocoyl betaine | 2.0 |
| Ethylhexyl glycerine | 1.0 |
| Myristyl alcohol | 1.0 |
| Sodium lauroyl glutamate | 2.0 |
| Polyquaternium-6 | 0.5 |
| Dimethicone | 0.5 |
| Ubiquinone | 0.1 |
| PEG-18 Glyceryl oleate/cocoate | 1.2 |
| PPG-9 | 0.8 |
| Citric acid/sodium hydroxide | q.s. to pH 5.0 |
| Preservative, fragrance | q.s |
| Water | to 100 |

EXAMPLE 13

| | % by weight |
|---|---|
| Sodium lauryl ether sulphate | 3.0 |
| Sodium lauryl ether carboxylate | 6.0 |
| Cocoyl polyglucoside | 3.0 |
| Cocoamphoacetate | 4.0 |
| Sodium cocyl glutamate | 2.0 |
| Ethylhexyl glycerine | 1.0 |
| Myristyl alcohol | 1.0 |
| Cocoyl betaine | 1.0 |
| Polyquaternium-7 | 0.8 |
| Dimethicone | 0.5 |
| PEG-90 glyceryl isostearate | 3.0 |
| PPG-12 | 0.6 |
| PPG-7 | 0.9 |
| Basic red 51 | 0.1 |
| Citric acid/sodium hydroxide | q.s. to pH 5.5 |
| Preservative, fragrance | q.s |
| Water | to 100 |

EXAMPLE 14

| | % by weight |
|---|---|
| Sodium lauryl ether sulfate | 9.0 |
| Laureth-16 | 3.0 |
| Cocoyl betaine | 2.0 |
| Sodium lauroyl glutamate | 2.0 |
| Ethylhexyl glycerine | 1.0 |
| Myristyl alcohol | 1.0 |
| Guarhydroxypropyltrimonium chloride | 1.0 |
| Sodium chloride | 1.3 |
| PPG-20 | 0.8 |
| Trimethyl pentaphenyl trisiloxane | 0.2 |
| Basic yellow 87 | 0.10 |
| Basic red 76 | 0.01 |
| Citric acid/sodium hydroxide | q.s. to pH 6.0 |
| Preservative, fragrance | q.s |
| Water | to 100 |

Increase of volume and an excellent golden blonde shine was observed on light blond hair. Conditioning effect in terms of manageability and soft feeling upon touching is excellent.

EXAMPLE 15

| | % by weight |
|---|---|
| Sodium lauryl ether sulfate | 3.0 |
| Sodium lauryl ether carboxylate | 7.0 |
| Laureth-16 | 3.0 |
| Cocoyl betaine | 2.0 |
| Sodium lauroyl glutamate | 2.0 |
| Ethylhexyl glycerine | 1.0 |
| Lauryl alcohol | 1.0 |
| Guarhydroxypropyltrimonium chloride | 1.0 |
| PEG-120 glyceryl stearate | 1.8 |
| PPG-7 | 1.8 |
| Dimethicone | 1.0 |
| Basic red 51 | 0.1 |
| Basic orange 31 | 0.05 |
| Citric acid/sodium hydroxide | q.s. to pH 5.7 |
| Preservative, fragrance | q.s |
| Water | to 100 |

An excellent red shine were observed on medium blond hair.

EXAMPLE 16

| | % by weight |
|---|---|
| Sodium lauryl ether sulphate | 10.0 |
| Laureth-16 | 3.0 |
| Cocoyl betaine | 2.0 |
| Sodium lauroyl glutamate | 2.0 |
| Polyquaternium-6 | 0.5 |
| Polysilicone-15 | 0.35 |
| Dimethicone | 0.5 |
| Ubiquinone | 0.1 |
| Sodium chloride | 1.0 |
| PPG-9 | 0.9 |
| Citric acid/sodium hydroxide | q.s. to pH 4.8 |
| Preservative, fragrance | q.s |
| Water | to 100 |

The above shampoo conditions hair excellently in terms of combability, softness, shine and elasticity and additionally gives fine hair excellent long lasting volume.

EXAMPLE 17

|  | % by weight |
| --- | --- |
| Sodium lauryl ether sulphate | 6.0 |
| Sodium lauryl ether carboxylate | 4.0 |
| Cocoyl glucoside | 3.0 |
| Cocamidopropyl betaine | 2.0 |
| Sodium lauroyl glutamate | 2.0 |
| Heptyl glycerine | 1.0 |
| Lauryl alcohol | 1.0 |
| Polyquaternium-6 | 0.5 |
| Benzophenone-4 | 0.5 |
| Dimethicone | 0.5 |
| Ubiquinone | 0.1 |
| PEG-18 glyceryl oleate/cocoate | 1.2 |
| PPG-9 | 2.0 |
| Citric acid/sodium hydroxide | q.s. to pH 5.5 |
| Preservative, fragrance | q.s |
| Water | to 100 |

The above shampoo conditions hair excellently in terms of combability, shine, softness and elasticity and additionally gives fine hair excellent long lasting volume.

EXAMPLE 18

|  | % by weight |
| --- | --- |
| Sodium lauryl ether sulphate | 15.0 |
| Decyl glucoside | 3.0 |
| Cocamidopropyl betaine | 2.0 |
| Sodium cocyl glutamate | 2.0 |
| Polyquaternium-6 | 0.5 |
| Decyl glycerine | 1.0 |
| Decyl alcohol | 1.0 |
| Ethylhexyl methoxy cinnamate | 0.3 |
| Dimethicone | 0.5 |
| Ubiquinone | 0.1 |
| Sodium chloride | 0.9 |
| PPG-9 | 0.7 |
| Citric acid/sodium hydroxide | q.s. to pH 5.2 |
| Preservative, fragrance | q.s |
| Water | to 100 |

EXAMPLE 19

|  | % by weight |
| --- | --- |
| Sodium lauryl ether sulphate | 10.0 |
| Cocyl glucoside | 5.0 |
| Lauryl betaine | 4.0 |
| Ethylhexyl glycerine | 1.0 |
| Myristyl alcohol | 1.0 |
| Sodium lauroyl glutamate | 2.0 |
| Polyquaternium-10 | 0.5 |
| Benzophenone-3 | 0.4 |
| Dimethicone | 0.5 |
| Sodium chloride | 1.0 |
| PPG-9 | 0.5 |
| Citric acid/sodium hydroxide | q.s. to pH 5.4 |
| Preservative, fragrance | q.s |
| Water | to 100 |

The invention claimed is:

1. An aqueous cleansing composition adapted to treat keratin fibres of human hair comprising:
    at least one amino acid surfactant selected from the group consisting of sodium cocoyl glutamate, sodium lauroyl glutamate and mixtures thereof and present at a concentration of 0.5 to 7.5% by weight;
    at least one glyceryl ether selected from the group consisting of glyceryl decyl ether, glyceryl ethylhexyl ether, glyceryl heptyl ether and mixtures thereof and present at a concentration of 0.5 to 5% by weight; and
    at least one fatty alcohol selected from the group consisting of decyl alcohol, lauryl alcohol, myristyl alcohol and mixtures thereof and present at a concentration of 0.5 to 2.5% by weight, all concentration values are calculated based on the total composition.

2. The aqueous cleansing composition according to claim 1, further comprising at least one non-ionic surfactant according to the general formula

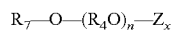

wherein $R_7$ is an alkyl group with 8 to 18 carbon atoms, $R_4$ is an ethylene or propylene group, Z is a saccharide group with 5 to 6 carbon atoms, n is a number from 0 to 10 and x is a number between 1 and 5.

3. The aqueous cleansing composition according to claim 1, further comprising at least one amphoteric surfactant selected from betaines, amidoalkyl betaines, sulfobetaines, and their mixtures.

4. The aqueous cleansing composition according to claim 1, further comprising at least one additional anionic surfactant, other than amino acid surfactant, that is present at a concentration of 2 to 25% by weight calculated to total composition.

5. The aqueous cleansing according to claim 1, further comprising at least one conditioning agent being a cationic polymer.

6. The aqueous cleansing according to claim 1, further comprising oily substances as conditioning agent selected from silicone oils, either volatile or non-volatile, natural and synthetic oils.

7. The aqueous cleansing according to claim 1, further comprising at least one UV filter.

8. The aqueous cleansing according to claim 1, further comprising at least one direct dye.

9. The aqueous cleansing composition according to claim 1, further comprising:
    Sodium laureth sulfate;
    Cocoamidopropyl betaine;
    Coco glucoside;
    Guar hydroxypropyl trimonium chloride;
    Bis(C13-15 alkoxy) PG-amodimethicone;
    Citric acid;
    Preservative and/or fragrance; and
    Water.

10. An aqueous cleansing composition adapted to treat keratin fibres of human hair comprising:
    at least one amino acid surfactant selected from the group consisting of sodium cocoyl glutamate, sodium lauroyl glutamate and mixtures thereof and present at a concentration of about 0.5 to about 4.0% by weight;
    at least one glyceryl ether selected from the group consisting of glyceryl decyl ether, glyceryl ethylhexyl ether and glyceryl heptyl ether and mixtures thereof and present at a concentration of about 0.5 to about 1.5% by weight; and
    at least one fatty alcohol selected from the group consisting of decyl alcohol, lauryl alcohol, myristyl alcohol and mixtures thereof and present at a concentration of about 0.5 to about 1% by weight, all concentration values are calculated based on the total composition.

11. An aqueous cleansing composition adapted to treat keratin fibres of human hair comprising:
- sodium lauroyl glutamate present at a concentration of about 0.5 to about 4.0% by weight;
- glyceryl ethylhexyl ether present at a concentration of about 0.5 to 5% by weight; and
- myristyl alcohol at a concentration of about 0.5 to 2.5% by weight, all concentration values are calculated based on the total composition.

* * * * *